US00PP24743P3

(12) United States Plant Patent
Carruth

(10) Patent No.: US PP24,743 P3
(45) Date of Patent: Aug. 12, 2014

(54) FLORIBUNDA ROSE PLANT NAMED 'WEKSTAMEDA'

(50) Latin Name: *Rosa hybrida*
Varietal Denomination: WEKstameda

(71) Applicant: Early Morning LLC, Pomona, CA (US)

(72) Inventor: Thomas F. Carruth, Altadena, CA (US)

(73) Assignee: Early Morning LLC, Pomona, CA (US)

( * ) Notice: Subject to any disclaimer, the term of this patent is extended or adjusted under 35 U.S.C. 154(b) by 114 days.

(21) Appl. No.: 13/694,324

(22) Filed: Nov. 19, 2012

(65) Prior Publication Data

US 2014/0143916 P1 May 22, 2014

(51) Int. Cl.
*A01H 5/00* (2006.01)

(52) U.S. Cl.
USPC ..... Plt./141; Plt./148

(58) Field of Classification Search
USPC ..... Plt./141, 148
See application file for complete search history.

(56) References Cited

U.S. PATENT DOCUMENTS

PP16,572 P3 5/2006 Carruth

*Primary Examiner* — Susan McCormick Ewoldt
(74) *Attorney, Agent, or Firm* — McKee, Voorhees & Sease, P.L.C.

(57) ABSTRACT

A new variety of Floribunda rose suitable for garden decoration, having flowers of clear lavender coloration.

1 Drawing Sheet

Classification: The present invention relates to a new *Rosa hybrida* plant.

Variety denomination: The new plant has the varietal denomination 'WEKstameda'.

BACKGROUND OF THE INVENTION

This invention relates to a new and distinct variety of Floribunda Rose. It has an undisseminated seedling of my creation as its seed parent with the following genetic origin {Stainless Steel×(Blueberry Hill×Stephen's Big Purple)}× Sunset Celebration and as its pollen parent the variety known as 'WEKblunez' (U.S. Plant Pat. No. 16,572).

SUMMARY OF THE INVENTION

Among the features which distinguish the new variety from other presently available and commercial rose cultivars known to the inventor are the following combinations of characteristics: its very double flowers of clear lavender coloration, its excellent color stability throughout the life of the flower, its large clusters and its very abundant bloom. The plant has a bushy rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKstameda' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, an undisseminated seedling of my creation by the following combination of characteristics: whereas 'WEKstameda' bears very double flowers (about 46 to 57 petals) of clear lavender coloration, the undisseminated seedling bears double flowers of light purple coloration with significantly lesser petalage (about 25 to 32 petals). The new variety has a bushy rounded medium height growing habit (about 130 to about 150 cm. in height), whereas the seed parent has a bushy upright significantly shorter growing habit (about 90 to about 100 cm. in height).

The new variety may be distinguished from its pollen parent, 'WEKblunez' by the following combination of characteristics: whereas 'WEKstameda' bears medium sized flowers (about 8.3 to about 9.1 cm. in diameter) of clear lavender coloration, 'WEKblunez' bears significantly larger flowers (about 10.0 to about 12.2 cm. in diameter) of orchid pink coloration. The flowers of the new variety have a slight citrus-like fragrance, whereas the flowers of the pollen parent have a strong old rose fragrance.

COMPARISON WITH THE CLOSEST COMMERCIALLY AVAILABLE CULTIVAR

The new variety may be distinguished from its closest commercially available cultivar, 'Angel Face' (U.S. Plant Pat. No. 2,792) by the following combination of characteristics: whereas 'WEKstameda' bears very double flowers (about 46 to 57 petals) of clear lavender coloration, 'Angel Face' bears double flowers of clear medium lavender coloration blushed ruby with significantly lesser petalage (about 25 to 30 petals). The new variety has a bushy rounded medium height growing habit (about 130 to about 150 cm. in height), whereas the closest commercially available cultivar has a rounded compact significantly shorter growing habit (about 90 to about 120 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of September. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of September. Phenotypic expression may vary with environmental, cultural and climatic conditions, as well as differences in conditions of light and soil.

FLOWER

The new variety usually bears its flowers in clusters of three to five or more per stem. Flowers are borne in regular somewhat flat to rounded clusters on strong medium length stems (about 20 to about 34 cm.). Outdoors, the plant blooms very abundantly and nearly continuously during the growing season. The flowers have a slight citrus-like fragrance.

BUD

The peduncle is about 4.1 to about 5.2 cm. in length, of average caliper (about 2.5 to about 3.5 cm. in diameter), and usually erect. It is moderately rough, with few stipitate glands and some very small prickles. Peduncle color is between 146C and 144A.

Before the calyx breaks, the bud is about 1.5 to about 1.9 cm. in diameter at the widest point, about 2.0 to about 2.3 cm. in length, and ovoid to somewhat pointed in shape. The surface of the bud bears between 5 to 7 foliaceous appendages, very few stipitate glands and usually with slender entire foliaceous parts extending beyond the tip of the bud about ½ or more of its length. Bud color is between 144A and 146B.

The sepals are about 2.0 to about 2.3 cm. in length and about 0.7 to about 0.9 cm. in width at the widest point. The outer surface color of the sepal is between 144A and 146B. The outer surface of the sepal is very smooth and bears between 1 to 4 foliacious appendages with very few stipitate glands. The inner surface color of the sepal is near 146D. The inner surface of the sepal is covered with fine wooly tomentum; sepal margins are lined with many stipitate glands and some hairs.

The receptacle of the flower is of somewhat short to medium length (about 0.6 to about 0.7 cm.) and average in caliper (about 0.9 to about 1.2 cm. in diameter). The receptacle is urn-shaped in form. Its surface is very smooth with few hairs and with moderately thick fleshy walls. The receptacle color is between 144A and 146B.

As the petals open (after the calyx breaks), the bud is about 2.2 to about 2.5 cm. in diameter at the widest point, about 2.6 to about 3.0 cm. in length, and moderately ovoid to nearly globular in form. The color of the under surfaces of the newly opened petals is between 70C and 70D sometimes blushed with as dark as 71B at the very edge of the petal. At the point where the petal attaches, there is a somewhat small zone of near 1D. The color of the upper surfaces of the newly opened petals is between 78D and 70D. At the point where the petal attaches, there is a moderately large zone of near 1C.

BLOOM

When fully open, the bloom ranges from about 8.3 to about 9.1 cm. in diameter. Petalage is very double with about 46 to 57 petals and about 5 to 9 petaloids irregularly arranged. When partially open, the bloom form is moderately cupped to somewhat high centered, and the petals are somewhat tightly spiraled to cupped with petal edges somewhat rolled outward. When fully open, the bloom form is more cupped, and the petals are loosely cupped to moderately undulated with petal edges moderately rolled outward.

PETALS

The substance of the petals is moderately heavy and of medium thickness, with upper surfaces somewhat satiny and under surfaces slightly shiny to matte. The petals are about 3.8 to about 4.6 cm. in length and about 2.8 to about 3.6 cm. in width at the widest point. Petal margins are usually entire to sometimes moderately crenate mostly on the outermost petals.

The outer petals are somewhat broadly obovate in shape with rounded to sometimes moderately crenate apices.

The inner petals are moderately obovate to nearly oblanceolate in shape with rounded apices.

Petaloids are about 2.1 to about 2.4 cm. in length and about 0.8 to about 1.3 cm. in width at the widest point. Petaloids are irregularly shaped somewhat obovate to oblanceolate with rounded apices.

NEWLY OPENED FLOWER

The under surface color of the outer, intermediate and inner petals is between 75C and 73D. At the point where the petal attaches, there is a somewhat small zone of near 158C.

The upper surface color of the outer, intermediate and inner petals is between 75B and 73C. At the point where the petal attaches, there is a moderately large zone of near 2D.

The under and upper surface colors of the petaloids are similar in coloration to the upper and under surfaces of the intermediate and inner petals.

The general tonality of the newly opened flower is between 75B and 73C.

THREE-DAY-OLD FLOWER

The under surface color of the outer, intermediate and inner petals is between 75D and 73D. At the point where the petal attaches, there is a somewhat small zone of near 158D.

The upper surface color of the outer, intermediate and inner petals is between 75C and 73D. At the point where the petal attaches, there is a moderately large zone of near 155C.

The under and upper surface colors of the petaloids are similar in coloration to the upper and under surfaces of the intermediate and inner petals.

The general tonality of the three-day-old flower is between 75C and 73D.

On the spent bloom, the petals usually drop off cleanly and are not particularly affected by cold, hot or dry weather.

In September in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 95) and are arranged regularly about the pistils; a few are mixed with petaloids. The filaments are medium to long in length (about 0.3 to about 0.8 cm.) most with anthers. Filaments are near 19C in color often moderately suffused with near 53B. The anthers are somewhat small to medium for the class and all open approximately at the same time. Anther color when immature is near 20A on the external part and near 20B on the internal part. Anther color at maturity is near 163A on the external part and near 166A on the internal part. Pollen is moderate to abundant and near 19D in color.

FEMALE REPRODUCTIVE ORGANS

Pistils vary in number (average about 140). The styles are somewhat uneven, moderately short in length (about 0.2 to about 0.3 cm.), somewhat thin to average in caliper, and moderately bunched. Stigma color is near 158A. Style color is near 45C. Ovaries are usually all enclosed in the calyx.

Hips are of somewhat short to average length (about 2.1 to about 2.5 cm.), somewhat ovoid to globular in form, and near 172D in color when ripe. The hip surface is very smooth with moderately thick fleshy walls. The sepals are moderately fugacious.

The seeds are irregularly rounded, smooth in texture, approximately 15 to about 18 per hip, about 0.4 to about 0.6 cm. in diameter at the widest point and near 164C in color.

FOLIAGE

The compound leaves are usually comprised of three to five leaflets and are borne abundantly. The five-leaflet leaves are about 10.2 to about 13.5 cm. in length and about 8.5 to about 12.8 cm. in width at the widest point, somewhat heavy to leathery in texture, and mostly matte to somewhat semi-glossy in finish on the upper side and matte in finish on the under side. The leaves have a pinnate venation pattern. The terminal leaflets are about 4.9 to about 7.1 cm. in length and about 3.4 to about 5.6 cm. in width at the widest point, shaped broadly ovate with moderately acute apices and rounded to somewhat inequilateral bases. Their margins are usually simply serrate.

The upper surface color of the mature leaf is between 137A and 147A. The under surface color of the mature leaf is near 148B sometimes moderately suffused with between 184D and 185C. The under and upper colors of the leaf veins on the mature leaf are similar in coloration to the upper and under surfaces colors of the mature leaf. The upper surface color of the young leaf is between 144A and 146C, usually heavily suffused with between 183A and 187A. The under surface color of the young leaf is between 144A and 146C, usually heavily suffused with between 183B and 187C. The under and upper colors of the leaf veins on the young leaf are similar in coloration to the upper and under surfaces colors of the young leaf.

The rachis is average to somewhat heavy in caliper and moderately rough. The upper side is moderately grooved with few hairs and some stipitate glands on the edges of the grooves. The under side of the rachis is moderately rough with some stipitate glands and few small prickle. The rachis color is near 146C on the under side and near 146B on the upper side.

The stipules are about 1.3 to about 1.5 cm. in length and of moderate width (about 0.2 to about 0.4 cm.) with medium length straight points that usually turn out at an angle of more than 45 degrees. The under and upper surface color of the stipule is between 146B and 146C.

The petiole is average to somewhat heavy in caliper and moderately rough. The upper side is moderately grooved with few hairs and some stipitate glands on the edges of the grooves. The under side of the petiole is moderately rough with some stipitate glands and few small prickle. The petiole is about 0.6 to about 0.9 cm. in length and about 0.2 to about 0.3 cm in width at the widest point. The petiole color is near 146C on the under side and near 146B on the upper side.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy rounded medium height growing habit (about 130 to about 150 cm. in height and about 70 to about 90 cm. spread at the widest point), with full branching. It displays moderately vigorous growth and the canes are of medium to heavy caliper for the class (about 0.9 to about 2.4 cm. in diameter at the widest point).

The color of the major stems is between 147B and 148A. They bear many large prickles that are about 0.6 to about 0.8 cm. in length. The large prickles are almost straight and angled slightly downward with a medium length moderately broad oval base; prickle color is near 166A. The major stem bears many small prickles of similar shape and coloration.

The color of the branches is between 146B and 146C. They bear many large prickles which are of similar size and shape to the large prickles on the major stems; prickle color is near 165A. The branches bear many small prickles of similar shape and coloration.

The color of the new shoots is between 146D and 138B often lightly suffused with 183B and 187C. They bear many large prickles which are of similar size and shape to the large prickles on the major stems; prickle color is between 165C and 163A. The shoots bear many small prickles of similar shape and coloration.

I claim:

1. A new and distinct Floribunda rose plant of the variety substantially as described and illustrated herein.

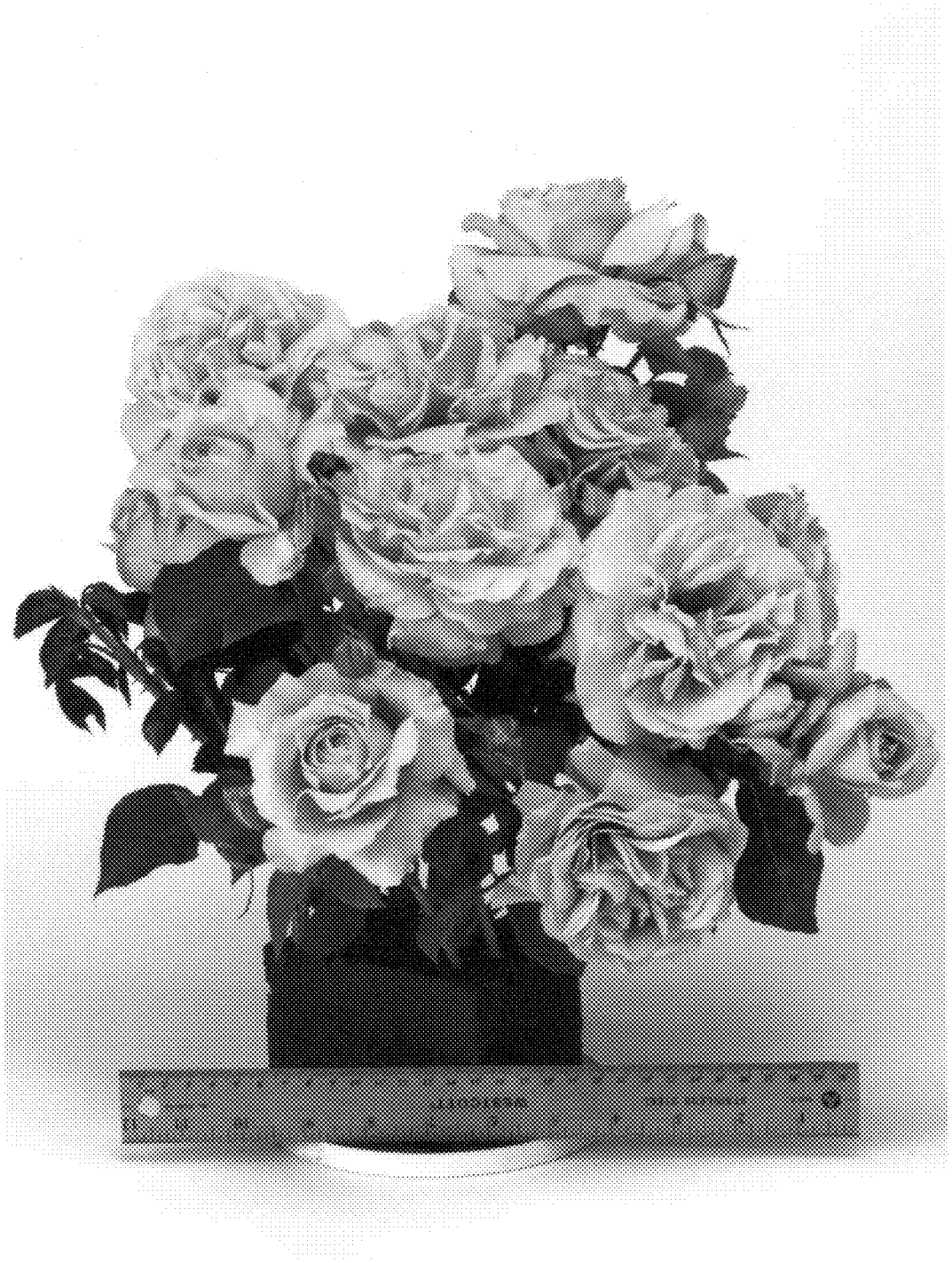

* * * * *